United States Patent
Lin et al.

(10) Patent No.: US 11,478,525 B2
(45) Date of Patent: Oct. 25, 2022

(54) **METHOD FOR PROMOTING GROWTH OF *AKKERMANSIA MUCINIPHILA* USING *MUSA* FERMENTS**

(71) Applicant: TCI CO., LTD., Taipei (TW)

(72) Inventors: Yung-Hsiang Lin, Taipei (TW); Chu-Han Huang, Taipei (TW); Cheng-Yu Ho, Taipei (TW)

(73) Assignee: TCI CO., LTD., Taipei (TW)

( * ) Notice: Subject to any disclaimer, the term of this patent is extended or adjusted under 35 U.S.C. 154(b) by 158 days.

(21) Appl. No.: 16/727,389

(22) Filed: Dec. 26, 2019

(65) Prior Publication Data

US 2021/0023159 A1 Jan. 28, 2021

(30) Foreign Application Priority Data

Jul. 22, 2019 (TW) .................................. 108125874

(51) Int. Cl.
| | | |
|---|---|---|
| *A61K 36/88* | (2006.01) | |
| *A61K 31/702* | (2006.01) | |
| *A61P 3/06* | (2006.01) | |
| *C12N 1/20* | (2006.01) | |

(52) U.S. Cl.
CPC ............ *A61K 36/88* (2013.01); *A61K 31/702* (2013.01); *A61P 3/06* (2018.01); *C12N 1/20* (2013.01)

(58) Field of Classification Search
None
See application file for complete search history.

(56) References Cited

U.S. PATENT DOCUMENTS

| | | | | |
|---|---|---|---|---|
| 2015/0306152 A1* | 10/2015 | Cani | ..................... | A61P 3/00 424/93.4 |
| 2016/0319358 A1* | 11/2016 | Apte | ..................... | G16B 20/20 |
| 2018/0055905 A1* | 3/2018 | Lin | ..................... | A23L 2/02 |

FOREIGN PATENT DOCUMENTS

| | | | |
|---|---|---|---|
| CN | 104886495 A | * | 9/2015 |
| CN | 109810931 A | | 5/2019 |
| TW | 201807193 A | | 3/2018 |

OTHER PUBLICATIONS

EngMT-Chen, C. et al. Preparation method of probiotic fermentation banana puree. Chinese Patent Application Publication No. CN104886495A; Sep. 9, 2015. pp. 1-17; specif. pp. 1,2, 4, 5.*
Depommier, C. et al. Jul. 1, 2019. Supplementation with Akkermansia muciniphila in overweight and obese human volunteers: a proof-of-concept exploratory study. Nature Medicine Letters 25: 1096-1103; specif. pp. 1096, 1101.*
Examination report dated Sep. 13, 2021, listed in correspondent China patent application No. 201910714710.3 (publication No. CN 112274577 A).
Effects of different probiotics on metabolic syndrome and intestinal flora in obese mice induced by high-fat diet., Zhao et al., Microbiomics and Precision Medicine, Shanghai Jiao Tong University Press Co., Ltd., Dec. 31, 2017 p. 492-493, second paragraph of p. 492 and second paragraph of p. 493.
Influence of different probiotic on lipid metabolism and LPS of high fat diet induced obese mice., Fang et al., vol. 23, No. 4, Chinese Journal of Laboratory Diagnosis, Apr. 30, 2019 p. 692-695, section 3.
Research progress on fecal microbiota transplantation for the improvement of obesity and type 2 diabetes melitus., Ge et al., vol. 22, No. 6, Parenteral & Enteral Nutrition, Nov. 30, 2015 p. 370-373, 377, last 1-2 lines in the left column of p. 371.
Research progress of Akkermansia muciniphila and its mechanism in obesity., Shen et al., vol. 38, No. 10, Basic & Clinical Medicine, Oct. 31, 2018 p. 1475-1479, first paragraph on the right column on p. 1475, section 1.3, 2.2 on the p. 1476.

* cited by examiner

*Primary Examiner* — Olivia M. Wise
*Assistant Examiner* — Sharon M. Papciak
(74) *Attorney, Agent, or Firm* — Chieh-Mei Wang

(57) ABSTRACT

Provided is a method of promoting the growth of *Akkermansia muciniphila*, including contacting *A. muciniphila* with an effective amount of a prebiotic composition including a *Musa* ferment. Also provided is a prebiotic composition including a *Musa* ferment. The prebiotic composition promotes the growth of *A. muciniphila* in the intestine, and reduces the body weight, fat percentage, waist circumference, and hip circumference of obese individuals.

5 Claims, 6 Drawing Sheets

Specification includes a Sequence Listing.

METHOD FOR PROMOTING GROWTH OF *AKKERMANSIA MUCINIPHILA* USING *MUSA* FERMENTS

CROSS-REFERENCE TO RELATED APPLICATION

This application claims priority of Taiwan patent application No. 108125874, filed on Jul. 22, 2019, the content of which is incorporated herein in its entirety by reference.

BACKGROUND OF THE INVENTION

1. Field of the Invention

The present invention relates to a prebiotic composition and applications thereof. Particularly, the present invention relates to a prebiotic composition including a *Musa* ferment and a method of promoting the growth of *Akkermansia muciniphila* by using the prebiotic composition.

2. The Prior Art

Numerous medical studies have shown that the intestinal environment is closely related to the maintenance of physical functions and disease prevention. The intestine is not only a digestive organ, but also a site where large numbers of immune cells reside to prevent pathogens from invasion into the body and where nerve branches largely extend to collect and send physiological information to the central nervous system. Therefore, intestinal health has a great impact on human health. In the past decade, research has found that more than a thousand intestinal bacteria species live in the intestinal mucosa. These bacteria communicate with the organs and give appropriate responses, such as supplying the nutrients required by the host, regulating intestinal cell development, and inducing the development of the immune system. Therefore, intestinal bacteria may be considered as an essential organ of the body.

Each member of the intestinal bacteria has its specific functions. When the composition of the intestinal bacteria is unbalance due to bad living habits, diseases, or use of antibiotics, individuals may lose health. For example, when one usually has a high-fat diet, Gram-negative bacteria in the large intestine that prefer to consume fat will multiply and produce lipopolysaccharides (LPS), which can cause chronic inflammation throughout the body through blood circulation, eventually leading to chronic diseases such as type 2 diabetes, cardiovascular diseases, and even neurodegenerative diseases and cancer. Studies have also shown that mice with disrupted intestinal bacterial composition have poor memory in stressful situations. Thus, the homeostasis of intestinal bacteria helps maintain physical and mental health.

Intestinal bacteria of the genus *Bifidobacterium* or *Lactobacillus* are currently known to benefit human health. In addition, *Akkermansia muciniphila* is also a potential probiotic. This species accounts for 1% to 4% of intestinal bacteria in adults, and it is an obligate anaerobic gram-negative bacterium that inhabits the large intestine and can utilize mucin as the sole nutrient source. *Akkermansia* has been reported to be involved in sugar and fat metabolisms, and intestinal immunity. Some studies have found that *Akkermansia* can produce short-chain fatty acids (such as acetic acid) from mucin and supply the required energy to intestinal goblet cells, thereby enhancing mucin production and thickening the intestinal mucus layer. In addition, the outer membrane protein Amuc-1100 of *Akkermansia* has been found to activate Toll-like receptor 2 (TLR2)-mediated intracellular signals in intestinal epithelial cells, thereby promoting the proliferation of epithelial cells. The effects of *Akkermansia* contribute to the integrity of the intestinal barrier, thus reducing the entry of harmful substances into the blood and lowering inflammatory responses. Studies also show that mice on a high-fat diet had lower blood LPS concentration, improved insulin resistance, and decreased fat accumulation after administered with *Akkermansia*.

Since *Akkermansia* is essential for maintenance of the intestinal health and possibly the physical and mental health, it is of necessity to develop a probiotic composition that promotes the growth of *Akkermansia* in the gut.

SUMMARY OF THE INVENTION

Accordingly, in one aspect, the present invention provides a method of promoting the growth of *Akkermansia muciniphila*, including contacting *A. muciniphila* with an effective amount of a prebiotic composition including a *Musa* ferment.

In one embodiment of the invention, the step of contacting *A. muciniphila* with an effective amount of the prebiotic composition may be accomplished by administering the prebiotic composition to a human subject orally, so that the components of the prebiotic composition are delivered through the gastrointestinal tract to the intestine, where the *A. muciniphila* inhabits.

In one embodiment of the invention, the *Musa* ferment is obtained by a first fermentation and a second fermentation of a mixture of *Musa* fruit flesh and water, wherein the first fermentation is carried out with *Streptococcus thermophilus* and *Saccharomyces cerevisiae*, and the second fermentation is carried out with *Acetobacter aceti*.

In one embodiment of the invention, the mixture of the *Musa* fruit flesh and water is prepared by mixing the *Musa* fruit flesh and water at a weight ratio ranging from 1:1 to 1:20; in the first fermentation, 0.1% to 0.4% (w/v) of the *S. thermophilus* and 0.2% to 0.5% (w/v) of the *S. cerevisiae* are inoculated, and 2% to 5% (w/v) of the *A. aceti* is inoculated in the second fermentation.

In one embodiment of the invention, the prebiotic composition further includes oligosaccharides selected from the group consisting of xylooligosaccharides, isomaltooligosaccharides, and combinations thereof. The prebiotic composition may further include a sugar alcohol. The sugar alcohol may be sorbitol, mannitol, erythritol, maltitol, lactitol, xylitol, or combinations thereof.

In one preferred embodiment, the prebiotic composition including the *Musa* ferment further includes xylooligosaccharides and lactitol, and the weight ratio of the *Musa* ferment, the xylooligosaccharides, and the lactitol is 3-5: 2-4: 2-4. In one most preferred embodiment, the weight ratio of the *Musa* ferment, the xylooligosaccharides, and the lactitol is 4:3:3.

In another aspect, the present invention provides a prebiotic composition for promoting the growth of *Akkermansia muciniphila*, including a *Musa* ferment, oligosaccharides, and a sugar alcohol, wherein the oligosaccharides are selected from xylooligosaccharides, isomaltooligosaccharides, and combinations thereof.

In still another aspect, the present invention provides a method of reducing the waist circumference in an obese subject, including administering to the subject an effective amount of the aforementioned prebiotic composition.

In one embodiment of the invention, the prebiotic composition increases the number of *A. muciniphila* in the intestine of the obese subject, and reduces the body weight, body or trunk fat percentage, waist circumference, and hip circumference of the obese subject.

The present invention discloses a variety of prebiotics and combinations thereof that benefit the growth of *A. muciniphila*. The combination of these prebiotics can be used to prepare a prebiotic composition that effectively promotes the growth of *A. muciniphila*, for example, a culture medium supplement for in vitro bacterial culture, or a prebiotic product that enhances *A. muciniphila* proliferation in the intestine of living subjects (such as in human). The prebiotic composition may be in the form of powders, granules, solutions, or capsules, and may be manufactured as a medicament, food, drink, or nutritional supplement that may be administered to a subject orally.

Since an appropriate number of *A. muciniphila* in the human intestinal tract can reduce chronic inflammation, improve sugar metabolism, and inhibit fat accumulation, the prebiotic composition of the present invention, by promoting growth of *A. muciniphila*, has the potential to alleviate or prevent metabolic diseases (such as diabetes), cardiovascular diseases (such as atherosclerosis), and aging-associated diseases (such as dementia).

The present invention is further explained in the following examples, in reference to the accompanying drawings. It should be understood that the examples given below do not limit the scope of the invention, and that modifications can be made without departing from the scope of the appended claims.

DETAILED DESCRIPTION OF THE PREFERRED EMBODIMENT

Figure 1:
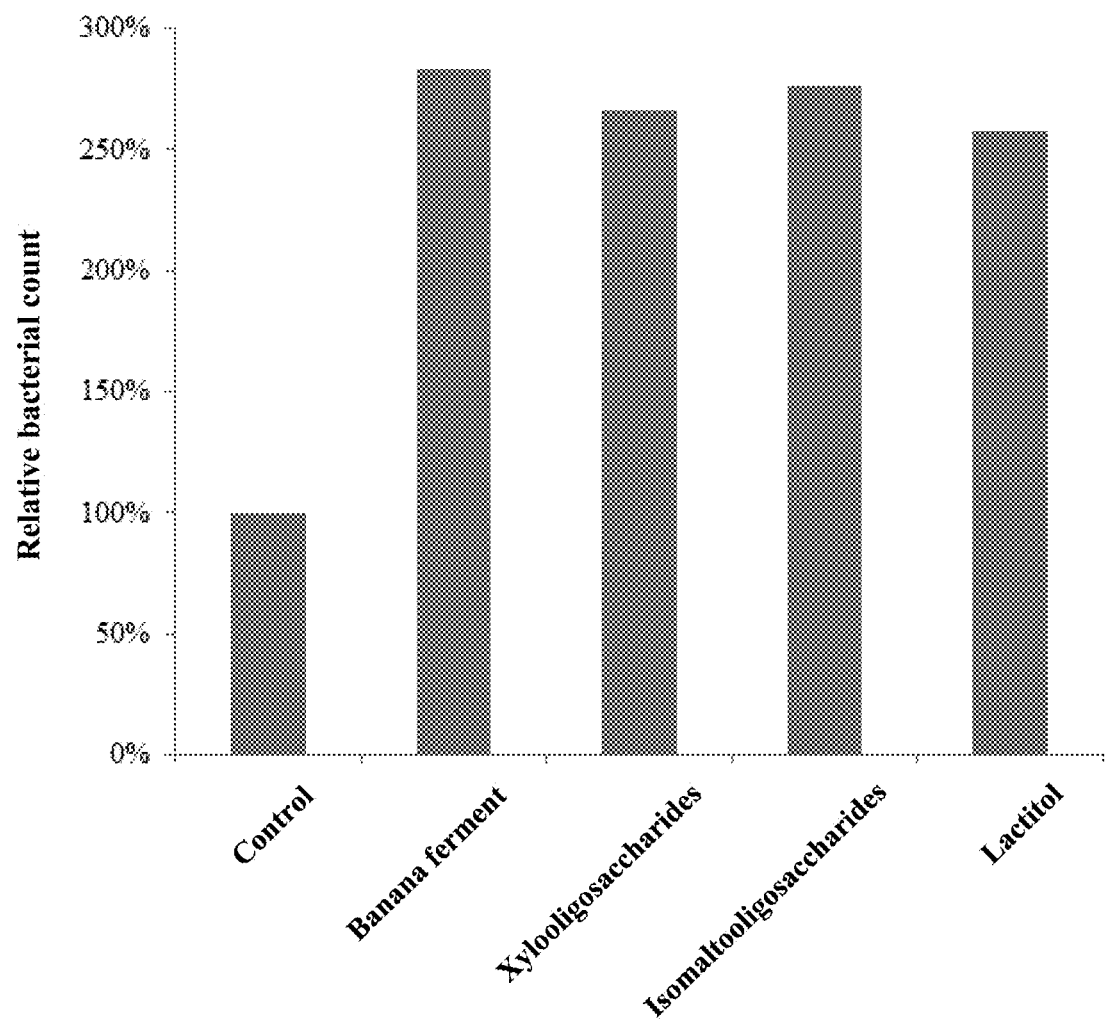
FIG. 1 shows the relative bacterial count of *Akkermansia muciniphila* after 48 hours of anaerobic incubation in a culture medium with or without a single candidate probiotic.

The present invention provides a method of promoting growth of *A. muciniphila*, including contacting the *A. muciniphila* with an effective amount of a prebiotic composition including a *Musa* ferment. In addition to the *Musa* ferment, the prebiotic composition may further include oligosaccharides selected from the group consisting of xylooligosaccharides, isomaltooligosaccharides, and combinations thereof, and a sugar alcohol such as sorbitol, mannitol, erythritol, maltitol, lactitol, and xylitol. The prebiotic composition preferably includes the *Musa* ferment, xylooligosaccharides, and lactitol, and the weight ratio of the *Musa* ferment, the xylooligosaccharides, and the lactitol is 3-5: 2-4: 2-4. The following examples show the promoting effects of the components of the prebiotic composition and their combinations on the growth of *A. muciniphila*, as well as the ability of the prebiotic composition to reduce the body weight, body or trunk fat percentage, waist circumference, and hip circumference of the obese subjects.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The term "*Musa*" as used herein refers to all species belonging to the *Musa* genus, including *Musa paradisiaca* (bananas, also known as plantains), *Musa acuminata*, and *Musa balbisiana*.

The term "xylooligosaccharides" as used herein refers to oligosaccharides containing 3 to 10 xylose units. They may be derived from plants, or prepared by microbial fermentation, enzyme transformation, or chemical synthesis.

The expression "an effective amount" as used herein refers to the amount of a composition required to elicit a particular effect in a subject. As appreciated by those skilled in the art, the effective amount will vary depending on the route of administration, the use of excipients, and the possible co-administration with other substances.

Materials and Methods

Preparation of *Musa* Ferments

*Musa* species are rich in phenols and pectin. Fermentation of *Musa* species will produce a ferment with more abundant constituents.

The *Musa* ferment used in Examples 1-3 is a banana ferment, the preparation of which is briefly described below. The banana fruit flesh and water are first mixed at a weight ratio of 1:1 to 1:20, preferably 1:1 to 1:5, to serve as a basal medium. After pasteurized, the basal medium is inoculated with *Streptococcus thermophilus* and *Saccharomyces cerevisiae* cells to obtain a first fermentation broth, and a first fermentation is carried out at 29° C. to 31° C. for 72 hours. In the first fermentation, 0.1% to 0.4% (w/v) of the *Streptococcus thermophilus* and 0.2% to 0.5% (w/v) of the *Saccharomyces cerevisiae* are inoculated. Thereafter, the first fermentation broth is inoculated with 0.5% to 1% (w/v) of *Acetobacter aceti*, and a second fermentation is carried out at 29° C. to 31° C. for 21 days to obtain the banana ferment. The banana ferment can be made into a powdery product by drying processes such as vacuum drying and spray drying.

In one embodiment, the *S. thermophilus* is the *S. thermophilus* BCRC 910636 strain (a deposited strain described in the Taiwan Patent I519644) purchased from Bioresource Collection and Research Center (BCRC) at the Food Industry Research and Development Institute. In another embodiment, the *S. cerevisiae* is the *S. cerevisiae* BCRC 21494 strain purchased from BCRC (also deposited under American Type Culture Collection (ATCC) 4126). In yet another embodiment, the *A. aceti* is the *A. aceti* BCRC 11688 strain purchased from BCRC (also deposited under ATCC 15973) or the *Acetobacter* BCRC 12324 strain.

Oligosaccharides, Polysaccharides and Sugar Alcohols

The oligosaccharides used in the Examples described herein include xylooligosaccharides (purchased from Shandong Longli Biotechnology Co., Ltd., China), isomaltooligosaccharides (purchased from Shandong Bailong Chuangyuan Biotechnology Co., Ltd., China), and fructooligosaccharides (purchased from MEIJI CO., Ltd). The polysaccharides used herein include inulin (purchased from Cosucra Groupe Warcoing SA). The sugar alcohols used herein include lactitol (purchased from Hongwei Biotechnology Co., Ltd, Taiwan), sorbitol, mannitol, erythritol, maltitol, and xylitol.

Bacterial Culture

The *Akkermansia muciniphila* used in the Examples described herein is the *Akkermansia muciniphila* BCRC 81048 strain purchased from BCRC at the Food Industry Research and Development Institute (also deposited under ATCC BAA-835). For subsequent use in the prebiotic test, the *A. muciniphila* strain, after thawed and activation, was inoculated at 3% and pre-cultured in BHI medium (15 g BD Difco Brain Heart Infusion broth (Thermo Fischer Scientific) dissolved in 1 L deionized water at a pH value of about 7.0) at 37° C. under an anaerobic condition (10% carbon dioxide, 10% hydrogen, and 80% nitrogen) for 48 hours.

Determination of Intestinal Bacterial Proportions

The feces of the participants were collected, and fecal genomic DNA samples were prepared using the Stool Genomic DNA Extraction kit (Biotools) according to the manufacturer's instructions. The DNA concentration of the samples was determined with a Nanodrop Spectrometer (Thermo Fisher Scientific). Thereafter, DNA content of each of the target bacteria in the samples was measured based on quantitative polymerase chain reaction (qPCR). Briefly, the DNA samples were subjected to qPCR on a PCR thermocycler (Step One Plus Real-Time PCR system; Applied Biosystems) using KAPA CYBR FAST qPCR Kit (2X) (KAPA Biosystems) and the primers for the indicative DNA sequences and the 16S ribosomal RNA (16S rRNA) gene of the target bacteria (Table 1). The cycle threshold ($C_T$) values were obtained for the indicative DNA sequences and the 16S rRNA gene of the target bacteria, and the difference between $C_T$ values was used to calculate fold change according to the $2^{-\Delta CT}$ formula. The proportion of a specific bacterial population in the intestine is expressed as a percentage and estimated as the ratio of the average fold change (obtained from repeated experiments) for a specific population's indicative DNA sequence to the sum of all populations' average fold changes.

TABLE 1

| Target bacteria | Nucleotide sequence of forward (F) and reverse (R) primers | SEQ ID NO |
|---|---|---|
| Firmicutes | F: GGAGYATGTGGTTTAATTCGAAGCA | 1 |
|  | R: AGCTGACGACAACCATGCAC | 2 |
| Bacteroidetes | F: GGARCATGTGGTTTAATTCGATGAT | 3 |
|  | R: AGCTGACGACAACCATGCAG | 4 |
| Proteobacteria | F: ACTCCTACGGGAGGCAGCAG | 5 |
|  | R: TCTACGRATTTCACCYCTAC | 6 |
| Actinobacteria | F: TACGGCCGCAAGGCTA | 7 |
|  | R: TCRTCCCCACCTTCCTCCG | 8 |
| Bifidobacteria | F: CGCGTCYGGTGTGAAAG | 9 |
|  | R: CCCCACATCCAGCATCCA | 10 |
| Lactobacillus | F: GAGGCAGCAGTAGGGAATCTTC | 11 |
|  | R: GGCCAGTTACTACCTCTATCCTTCTTC | 12 |
| Alistipes | F: ACGGCTCACCAAGGCTACGATACATAG | 13 |
|  | R: CCTCCGTATTACCGCGGCTGCT | 14 |
| Prevotella | F: TCGTGGGGTCGGGTTGCAGACC | 15 |
|  | R: CAGTTGCCATCGGGTGATGCCG | 16 |
| Faecalibacterium prausnitzii | F: CCATGAATTGCCTTCAAAACTGTT | 17 |
|  | R: GAGCCTCAGCGTCAGTTGGT | 18 |
| A. muciniphila | F: GCGGACGGCACATGATACTGCGAG | 19 |
|  | R: GCTTAACGCGTTAGCTCCGGCAC | 20 |
| Fusobacterium nucleatum | F: GCGCGTCTAGGTGGTTATGTAAGTCTGATGTG | 21, 22 |
|  | R: TTTGCTACCCACGCTTTCGCGC |  |
| Roseburia hominis | F: TGCAAGTCGAACGAAGC | 23 |
|  | R: CGGCTACTGATCGTCG | 24 |
| Clostridium difficile | F: GGTAAAGAGCGGCGGACGGG | 25 |
|  | R: CTGATCGTCGCCTTGGTAAGCCG | 26 |
| Helicobacter pylori CagA gene | F: GCGGGACAAGCAGCTAGCCC | 27 |
|  | R: GCTGATCGCCCTGCTCCAC | 28 |
| Conservative sequence of 16S rRNA gene | F: ACTCCTACGGGAGGCAGCAG | 29 |
|  | R: ATTACCGCGGCTGCTGG | 30 |

EXAMPLE 1

Prebiotic Test for *A. muciniphila*

In order to identify the nutrients beneficial to the growth of *A. muciniphila*, pre-cultured *A. muciniphila* was inoculated at 3% in BHI medium containing 1% (w/w) of the candidate prebiotics and incubated at 37° C. under anaerobic conditions for 48 hours. The bacterial culture was then spread on BHI agar plates and incubated for 72 hours for bacterial counting. The candidate prebiotic was selected from xylooligosaccharides, isomaltooligosaccharides, lactitol, inulin, fructooligosaccharides, and a banana ferment. For comparison, *A. muciniphila* was alternatively incubated in BHI medium without candidate prebiotics (control group).

FIG. 1 shows the effects of the various candidate prebiotics on the growth of *A. muciniphila*; and the relative bacterial count for the control group was defined as 100%. According to FIG. 1, the prebiotics that significantly increased the bacteria count, compared with the control group, include the banana ferment, xylooligosaccharides, isomaltooligosaccharides, and lactitol, which resulted in the relative bacterial counts of about 283%, 266%, 276%, and 258%, respectively. In contrast, inulin and fructooligosaccharides, well-known to promote the growth of *Lactobacillus* and *Bifidobacteria*, respectively, cannot significantly enhance the growth of *A. muciniphila*, and the relative bacterial counts after applications of these two sugars were about 110% (data not shown). The results indicate that each of the banana ferment, xylooligosacchandes, isomaltooligosaccharides, and lactitol can be used as prebiotics for *A. muciniphila*, but not any prebiotics beneficial for the *Lactobacillus* (such as fructooligosaccharides and inulin) can effectively promote the growth of *A. muciniphila*.

EXAMPLE 2

Prebiotic Composition for Promoting Growth of *A. muciniphila*

In order to assess the promoting effect of different combinations of the aforementioned *A. muciniphila* prebiotics on the growth of *A. muciniphila*, pre-cultured *A. muciniphila* was inoculated at 3% in BHI medium supplemented with different prebiotic compositions and incubated at 37° C. under anaerobic conditions for 48 hours. The bacterial culture was then spread on BHI agar plates and incubated for 72 hours for bacterial counting. The constituents (w/w %) for each prebiotic compositions added to the BHI medium are provided below: (a) 0.25% banana ferment, 0.25% isomaltooligosaccharides, 0.25% xylooligosaccharides, and 0.25% lactitol; (b) 0.4% banana ferment, 0.3% xylooligosaccharides, and 0.3% lactitol; (c) 0.4% banana ferment, 0.3% isomaltooligosaccharides, and 0.3% lactitol; or (d) 0.4% banana ferment, 0.3% isomaltooligosaccharides, and 0.3% xylooligosaccharides. For comparison, *A. muciniphila* was alternatively incubated in BHI medium without prebiotics (control group).

Figure 2:
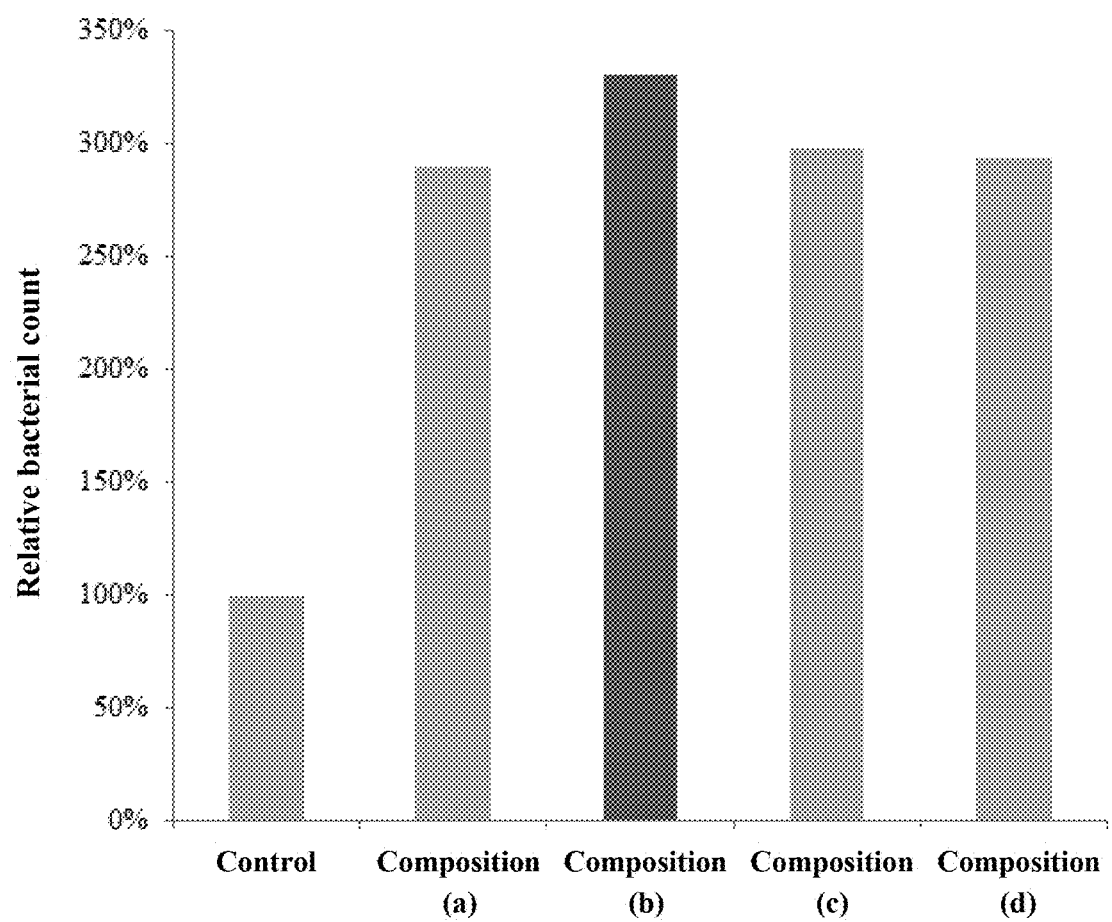
FIG. 2 shows the relative bacterial count of *A. muciniphila* after 48 hours of anaerobic incubation in a culture medium with or without the indicated prebiotic composition.

FIG. 2 shows the effects of the aforementioned prebiotic combinations on the growth of *A. muciniphila*; and the relative bacterial count for the control group was defined as 100%. According to FIG. 2, the addition of the prebiotic composition (a), (b), (c), or (d) to the medium significantly increased the relative counts of *A. muciniphila* to approximately 289%, 331%, 298%, and 294%, respectively, compared with the control group. Particularly, the combination of the banana ferment, xylooligosaccharides, and lactitol promotes the growth of *A. muciniphila* most effectively at the weight ratio of 3-5: 2-4: 2-4, even though lactitol was least effective in promoting growth as shown in FIG. 1.

EXAMPLE 3

Physiological Effects of the Prebiotic Composition

In this example, the physiological effects of continuous administration of the prebiotic composition described herein on obese participants were investigated. Seven obese participants aged 20 to 55 (including male and female) were orally administered for four weeks a prebiotic composition in capsule form containing 200 mg of banana ferment, 150 mg of xylooligosaccharides, and 150 mg of lactitol (i.e., daily dosage of 500 mg/per person/per day) after lunch. These participants were examined before and after four weeks for the proportion of *A. muciniphila* in the intestine. In addition, a body composition monitor (TANITA BC-601FS) was used to measure the body weight, body fat percentage, trunk fat percentage, waist circumference, and hip circumference. The obese participants are individuals with a body mass index (BMI) greater than 24 and a body fat percentage greater than 25% (for male) or greater than 30% (for female).

Figure 3A:
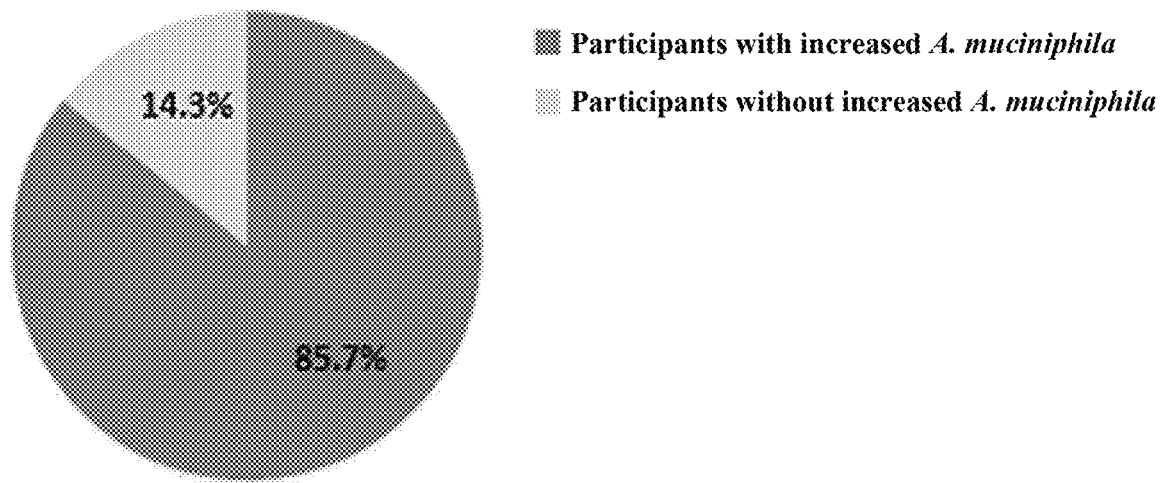
FIG. 3A shows the percentage of the subjects with or without increased proportion of *A. muciniphila* in the intestinal tract after administration for four weeks of a prebiotic composition according to one embodiment of the present invention.
Figure 3B:
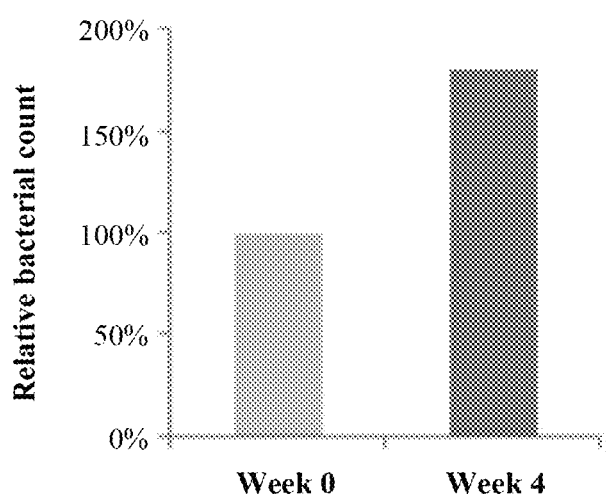
FIG. 3B shows the relative bacterial count of *A. muciniphila* in the intestine of the subjects shown in FIG. 3A that had increased proportion of *A. muciniphila*.
Figure 4:
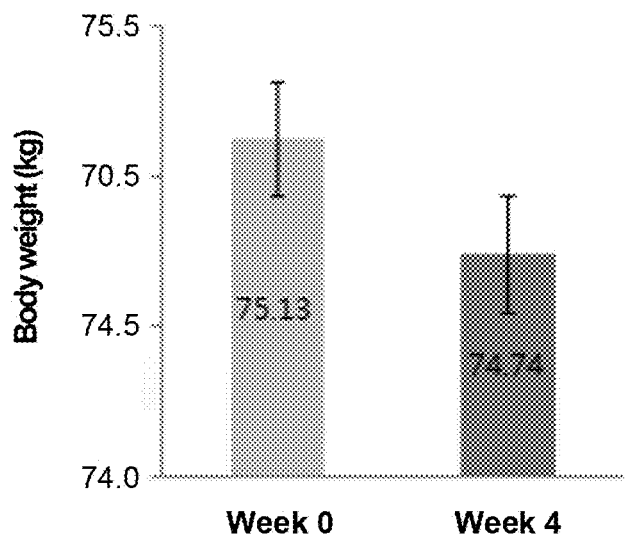
FIG. 4 shows the change in the body weight of participants after administration for four weeks of a prebiotic composition according to one embodiment of the present invention.
Figure 5:
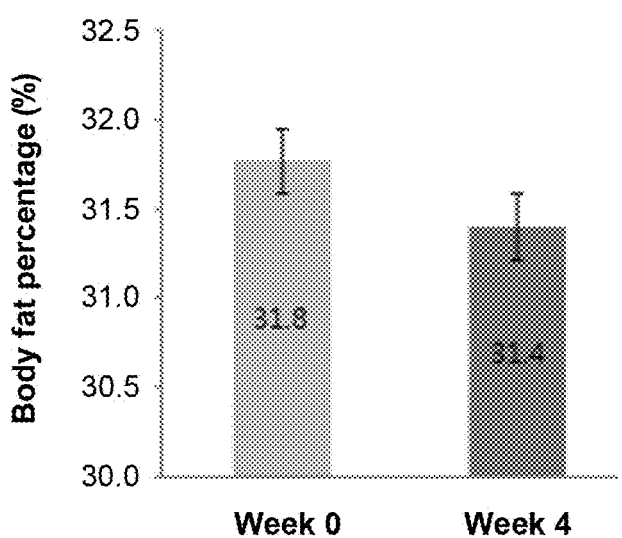
FIG. 5 shows the change in the body fat percentage of participants after administration for four weeks of a prebiotic composition according to one embodiment of the present invention.
Figure 6:
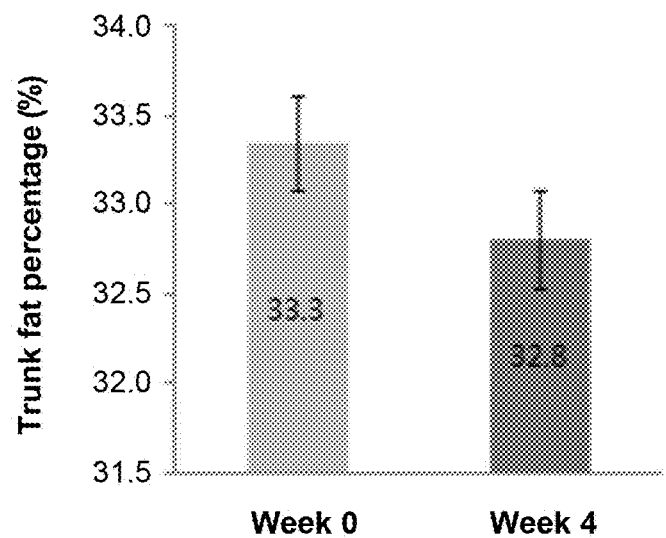
FIG. 6 shows the change in the trunk fat percentage of participants after administration for four weeks of a prebiotic composition according to one embodiment of the present invention.
Figure 7:
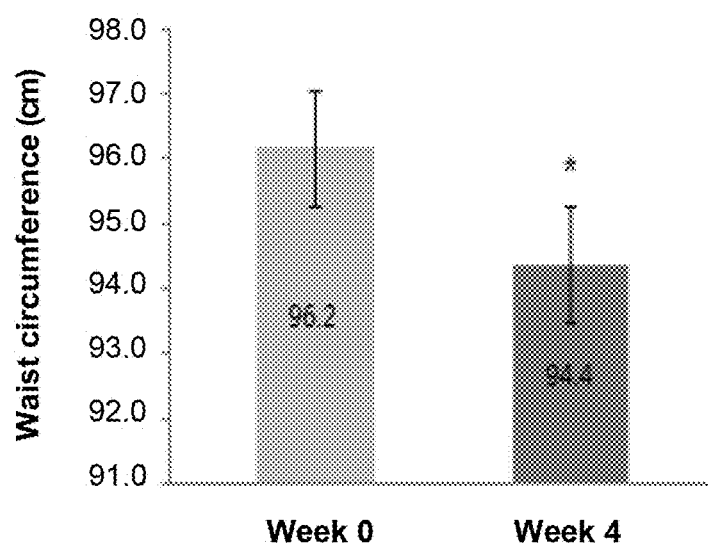
FIG. 7 shows the change in the waist circumference of participants after administration for four weeks of a prebiotic composition according to one embodiment of the present invention.
Figure 8:
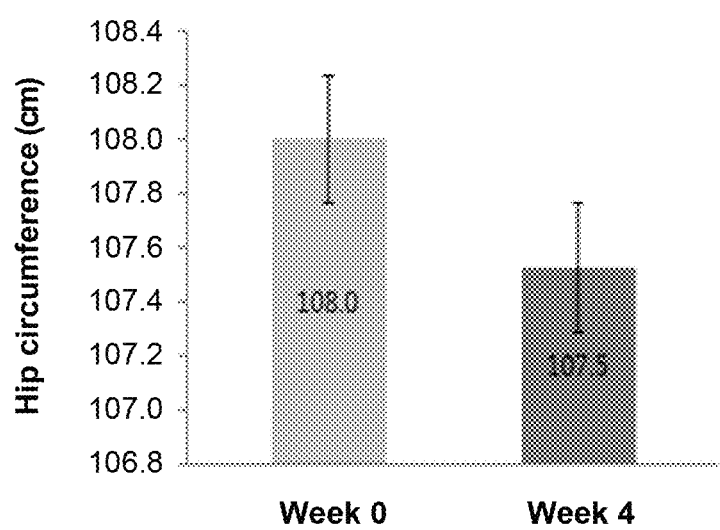
FIG. 8 shows the change in the hip circumference of participants after administration for four weeks of a prebiotic composition according to one embodiment of the present invention.

According to FIGS. 3A and 3B, 85.7% of the participants were found to have a significantly increased proportion of *A. muciniphila* in the intestine after administration of the prebiotic composition for four weeks, and the number of *A. muciniphila* increased by about 80% with respect to before the administration. The results demonstrate that the prebiotic composition described herein can promote the growth of *A. muciniphila* in the intestine of living subjects.

According to FIG. 4 to FIG. 8, administration of the prebiotic composition for four weeks cause, on average, a decrease of approximately 0.39 kg in the body weight, a decrease of about 0.4% in the body fat percentage, a significant decrease of about 0.5% in the trunk fat percentage, a significant decrease of approximately 1.8 cm in the waist circumference, and a significant decrease of about 0.5 cm in the hip circumference, compared with before administration. The results show that long-term use of the prebiotic composition of the present invention can improve physical conditions of obese subjects.

In conclusion, the present invention discloses a variety of prebiotics and combinations thereof that benefit the growth of *A. muciniphila*. The combination of these prebiotics can be used to prepare a prebiotic composition that effectively promotes the growth of *A. muciniphila*, for example, a culture medium supplement for in vitro bacterial culture, or a prebiotic product that enhances *A. muciniphila* proliferation in the human intestine. The prebiotic composition may be in the form of powders, granules, solutions, or capsules, and may be manufactured as a medicament, food, drink, or nutritional supplement that may be administered to a subject orally.

The present invention has been described with reference to the above preferred embodiments. However, it will be apparent to those skilled in the art that modifications and changes in form and detail may be made without departing from the scope of the present invention defined by the appended claims.

What is claimed is:

1. A method of promoting the growth of *Akkermansia muciniphila*, comprising contacting the *A. muciniphila* with an effective amount of a prebiotic composition comprising a *Musa* ferment, oligosaccharides, and a sugar alcohol, wherein the oligosaccharides are xylooligosaccharides, the sugar alcohol is lactitol, and the weight ratio of the *Musa* ferment, the xylooligosaccharides, and the lactitol is 4:3:3.

2. The method of claim 1, wherein the *Musa* ferment is obtained by a first fermentation and a second fermentation of a mixture of *Musa* fruit flesh and water, wherein the first fermentation is carried out with *Streptococcus thermophilus* and *Saccharomyces cerevisiae*, and the second fermentation is carried out with *Acetobacter aceti*.

3. The method of claim 2, wherein the mixture of the *Musa* fruit flesh and water is prepared by mixing the *Musa* fruit flesh and water at a weight ratio ranging from 1:1 to 1:20.

4. The method of claim 2, wherein 0.1% to 0.4% (w/v) of the *S. thermophilus* and 0.2% to 0.5% (w/v) of the *S. cerevisiae* are inoculated into the first fermentation, and wherein 2% to, and 2% to 5% (w/v) of the *A. aceti* is inoculated into the second fermentation.

5. A prebiotic composition for promoting the growth of *Akkermansia muciniphila*, comprising a *Musa* ferment, oligosaccharides, and a sugar alcohol, wherein the oligosaccharides are xylooligosaccharides, the sugar alcohol is lactitol, and the weight ratio of the *Musa* ferment, the xylooligosaccharides, and the lactitol is 4:3:3.

* * * * *

SEQUENCE LISTING

```
<160> NUMBER OF SEQ ID NOS: 30

<210> SEQ ID NO 1
<211> LENGTH: 25
<212> TYPE: DNA
<213> ORGANISM: Artificial sequence
<220> FEATURE:
<223> OTHER INFORMATION: PCR primer

<400> SEQUENCE: 1
```
ggagyatgtg gtttaattcg aagca                                            25

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2
agctgacgac aaccatgcac                                                  20

<210> SEQ ID NO 3
<211> LENGTH: 25
<212> TYPE: DNA
<213> ORGANISM: Artificial sequence
<220> FEATURE:
<223> OTHER INFORMATION: PCR primer

<400> SEQUENCE: 3
ggarcatgtg gtttaattcg atgat                                            25

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4
agctgacgac aaccatgcag                                                  20

<210> SEQ ID NO 5
<211> LENGTH: 20
<212> TYPE: DNA
<213> ORGANISM: Artificial sequence
<220> FEATURE:
<223> OTHER INFORMATION: PCR primer

<400> SEQUENCE: 5
actcctacgg gaggcagcag                                                  20

<210> SEQ ID NO 6
<211> LENGTH: 20
<212> TYPE: DNA
<213> ORGANISM: Artificial sequence
<220> FEATURE:
<223> OTHER INFORMATION: PCR primer

<400> SEQUENCE: 6
tctacgratt tcaccyctac                                                  20

<210> SEQ ID NO 7
<211> LENGTH: 16
<212> TYPE: DNA
<213> ORGANISM: Artificial sequence
<220> FEATURE:
<223> OTHER INFORMATION: PCR primer

<400> SEQUENCE: 7
tacggccgca aggcta                                                      16

<210> SEQ ID NO 8
<211> LENGTH: 19
<212> TYPE: DNA

```
<213> ORGANISM: Artificial sequence
<220> FEATURE:
<223> OTHER INFORMATION: PCR primer

<400> SEQUENCE: 8
tcrtccccac cttcctccg                                                      19

<210> SEQ ID NO 9
<211> LENGTH: 17
<212> TYPE: DNA
<213> ORGANISM: Artificial sequence
<220> FEATURE:
<223> OTHER INFORMATION: PCR primer

<400> SEQUENCE: 9
cgcgtcyggt gtgaaag                                                        17

<210> SEQ ID NO 10
<211> LENGTH: 18
<212> TYPE: DNA
<213> ORGANISM: Artificial sequence
<220> FEATURE:
<223> OTHER INFORMATION: PCR primer

<400> SEQUENCE: 10
ccccacatcc agcatcca                                                       18

<210> SEQ ID NO 11
<211> LENGTH: 22
<212> TYPE: DNA
<213> ORGANISM: Artificial sequence
<220> FEATURE:
<223> OTHER INFORMATION: PCR primer

<400> SEQUENCE: 11
gaggcagcag tagggaatct tc                                                  22

<210> SEQ ID NO 12
<211> LENGTH: 27
<212> TYPE: DNA
<213> ORGANISM: Artificial sequence
<220> FEATURE:
<223> OTHER INFORMATION: PCR primer

<400> SEQUENCE: 12
ggccagttac tacctctatc cttcttc                                             27

<210> SEQ ID NO 13
<211> LENGTH: 27
<212> TYPE: DNA
<213> ORGANISM: Artificial sequence
<220> FEATURE:
<223> OTHER INFORMATION: PCR primer

<400> SEQUENCE: 13
acggctcacc aaggctacga tacatag                                             27

<210> SEQ ID NO 14
<211> LENGTH: 22
<212> TYPE: DNA
<213> ORGANISM: Artificial sequence
<220> FEATURE:
<223> OTHER INFORMATION: PCR primer

<400> SEQUENCE: 14
cctccgtatt accgcggctg ct                                                  22
```

<210> SEQ ID NO 15
<211> LENGTH: 22
<212> TYPE: DNA
<213> ORGANISM: Artificial sequence
<220> FEATURE:
<223> OTHER INFORMATION: PCR primer

<400> SEQUENCE: 15
tcgtggggtc gggttgcaga cc                                          22

<210> SEQ ID NO 16
<211> LENGTH: 22
<212> TYPE: DNA
<213> ORGANISM: Artificial sequence
<220> FEATURE:
<223> OTHER INFORMATION: PCR primer

<400> SEQUENCE: 16
cagttgccat cgggtgatgc cg                                          22

<210> SEQ ID NO 17
<211> LENGTH: 24
<212> TYPE: DNA
<213> ORGANISM: Artificial sequence
<220> FEATURE:
<223> OTHER INFORMATION: PCR primer

<400> SEQUENCE: 17
ccatgaattg ccttcaaaac tgtt                                        24

<210> SEQ ID NO 18
<211> LENGTH: 20
<212> TYPE: DNA
<213> ORGANISM: Artificial sequence
<220> FEATURE:
<223> OTHER INFORMATION: PCR primer

<400> SEQUENCE: 18
gagcctcagc gtcagttggt                                             20

<210> SEQ ID NO 19
<211> LENGTH: 24
<212> TYPE: DNA
<213> ORGANISM: Artificial sequence
<220> FEATURE:
<223> OTHER INFORMATION: PCR primer

<400> SEQUENCE: 19
gcggacggca catgatactg cgag                                        24

<210> SEQ ID NO 20
<211> LENGTH: 23
<212> TYPE: DNA
<213> ORGANISM: Artificial sequence
<220> FEATURE:
<223> OTHER INFORMATION: PCR primer

<400> SEQUENCE: 20
gcttaacgcg ttagctccgg cac                                         23

<210> SEQ ID NO 21
<211> LENGTH: 32
<212> TYPE: DNA
<213> ORGANISM: Artificial sequence
<220> FEATURE:

<223> OTHER INFORMATION: PCR primer

<400> SEQUENCE: 21
gcgcgtctag gtggttatgt aagtctgatg tg					32

<210> SEQ ID NO 22
<211> LENGTH: 22
<212> TYPE: DNA
<213> ORGANISM: Artificial sequence
<220> FEATURE:
<223> OTHER INFORMATION: PCR primer

<400> SEQUENCE: 22
tttgctaccc acgctttcgc gc					22

<210> SEQ ID NO 23
<211> LENGTH: 17
<212> TYPE: DNA
<213> ORGANISM: Artificial sequence
<220> FEATURE:
<223> OTHER INFORMATION: PCR primer

<400> SEQUENCE: 23
tgcaagtcga acgaagc					17

<210> SEQ ID NO 24
<211> LENGTH: 16
<212> TYPE: DNA
<213> ORGANISM: Artificial sequence
<220> FEATURE:
<223> OTHER INFORMATION: PCR primer

<400> SEQUENCE: 24
cggctactga tcgtcg					16

<210> SEQ ID NO 25
<211> LENGTH: 20
<212> TYPE: DNA
<213> ORGANISM: Artificial sequence
<220> FEATURE:
<223> OTHER INFORMATION: PCR primer

<400> SEQUENCE: 25
ggtaaagagc ggcggacggg					20

<210> SEQ ID NO 26
<211> LENGTH: 23
<212> TYPE: DNA
<213> ORGANISM: Artificial sequence
<220> FEATURE:
<223> OTHER INFORMATION: PCR primer

<400> SEQUENCE: 26
ctgatcgtcg ccttggtaag ccg					23

<210> SEQ ID NO 27
<211> LENGTH: 20
<212> TYPE: DNA
<213> ORGANISM: Artificial sequence
<220> FEATURE:
<223> OTHER INFORMATION: PCR primer

<400> SEQUENCE: 27
gcgggacaag cagctagccc					20

```
<210> SEQ ID NO 28
<211> LENGTH: 19
<212> TYPE: DNA
<213> ORGANISM: Artificial sequence
<220> FEATURE:
<223> OTHER INFORMATION: PCR primer

<400> SEQUENCE: 28
gctgatcgcc ctgctccac                                                   19

<210> SEQ ID NO 29
<211> LENGTH: 20
<212> TYPE: DNA
<213> ORGANISM: Artificial sequence
<220> FEATURE:
<223> OTHER INFORMATION: PCR primer

<400> SEQUENCE: 29
actcctacgg gaggcagcag                                                  20

<210> SEQ ID NO 30
<211> LENGTH: 17
<212> TYPE: DNA
<213> ORGANISM: Artificial sequence
<220> FEATURE:
<223> OTHER INFORMATION: PCR primer

<400> SEQUENCE: 30
attaccgcgg ctgctgg                                                     17
```